United States Patent [19]

Granberg

[11] Patent Number: 4,664,101

[45] Date of Patent: May 12, 1987

[54] OPEN FRAME TRACTION SYSTEM

[76] Inventor: Elof Granberg, 15 Harbor View Ct., San Rafael, Calif. 94901

[21] Appl. No.: 825,308

[22] Filed: Feb. 3, 1986

[51] Int. Cl.[4] ............................ A61F 5/00; A61F 5/04

[52] U.S. Cl. ................................ 128/84 R; 128/84 C; 128/71

[58] Field of Search .................. 128/70, 71, 75, 84 R, 128/84 C, 87 B

[56] References Cited

U.S. PATENT DOCUMENTS

| | | | |
|---|---|---|---|
| 2,377,940 | 6/1945 | Hughes | 128/75 X |
| 2,865,367 | 12/1958 | Sorenson | 128/71 |
| 3,276,444 | 10/1966 | Rice | 128/75 |
| 3,856,003 | 12/1974 | Pfluger | 128/75 |
| 3,888,243 | 6/1975 | Powlan | 128/75 |
| 4,114,611 | 9/1978 | Lyle et al. | 128/84 C X |
| 4,356,816 | 11/1982 | Granberg | 128/71 |
| 4,362,151 | 12/1982 | Cottrell | 128/75 |
| 4,466,427 | 8/1984 | Granberg | 128/71 |

OTHER PUBLICATIONS

Lossing Orthopedic Company brochure on Backtrac and Necktrac.

*Primary Examiner*—Robert A. Hafer
*Assistant Examiner*—Kathleen J. D'Arrigo
*Attorney, Agent, or Firm*—Townsend and Townsend

[57] ABSTRACT

A portable traction system includes an open frame for mounting directly on a bed, treatment table, or the floor. A tension-applying mechanism is mounted on the frame and attached to a cervical tension cord and a pelvic tension cord. The cervical tension cord is threaded to one end of the frame and extends upward on a vertical post, allowing the patient to undergo cervical traction. The pelvic traction cord extends to the opposite end of the frame and is connected to a pelvic traction belt which goes around the patient's waist. The patient wears a counterbelt attached to the first end of the frame, and may use the system to undergo pelvic traction. Use of the system does not require specialized mounting equipment, and may be utilized by simply placing the frame on a bed, treatment table, or other surface.

15 Claims, 7 Drawing Figures

OPEN FRAME TRACTION SYSTEM

BACKGROUND OF THE INVENTION

1. Field of the Invention

The present invention relates generally to traction systems, and in particular to a portable traction system having an open frame which may be mounted directly on a bed, treatment table, floor, or other flat surface.

In most modern hospitals, traction is applied to a patient using an electrically controlled winch systems which may be mounted on specially constructed beds having the necessary mounting hardware. Such traction winch systems and the mounting-compatible beds are quite expensive and generally not suitable for home and other out-patient use. Moreover, such traction systems are not portable and cannot easily be transported to remote locations where, in emergencies, the availability of traction equipment may be critical.

For these reasons, it would be desirable to provide inexpensive, portable traction systems suitable for home and emergency use, where the traction systems may be mounted directly on conventional beds, floors, or other flat surfaces. In particular, it would be desirable to provide such equipment capable of providing both cervical and pelvic traction wherein the patient will be able to manually actuate the system to provide a preselected tension force for the traction. Finally, it would be desirable that the system be fail-safe in that it would be virtually impossible for the system to apply a traction force greater than the force set into the system.

2. Description of the Background Art

U.S. Pat. Nos. 4,356,816 and 4,466,427, issued to the inventor herein, describe portable traction devices employing manually-actuated tension systems. The tension system described in the '427 patent is substantially the same as the system employed by the traction device of the present invention. Floor and bed mounted devices for applying cervical or pelvic traction to a patient are available from the Lossing Orthopedic Company, 2217 Nicollet Avenue South, Minneapolis, Minn. 55404 under the trade names Backtrac® and Necktrac®. Some of the devices employ free-standing frames which may be mounted on a floor or bed. One of the devices is described in U.S. Pat. No. 4,362,151. U.S. Pat. Nos. 3,856,003 and 3,276,444 describe free weight systems for applying cervical traction, where the systems are detachably mounted on patient beds.

SUMMARY OF THE INVENTION

The present invention provides a portable traction system which may be utilized in conjunction with home beds, treatment tables, and other flat surfaces which are not specially adapted for the mounting of traction equipment. The traction system comprises a rigid frame having a central opening large enough to allow a patient to recline inside the frame. Thus, the frame may be mounted on top of an ordinary bed or other flat surface, such as a carpeted floor, and the patient may lie down inside of the frame for treatment. The system further includes both a cervical harness attached to a tension cord, and a pelvic harness attached to a separate tension cord. A tension-applying mechanism, typically a hydraulic cylinder, is mounted along one side of the frame, and pulleys or other mechanisms are provided on the frame for threading the tension cords to opposite ends of the frame. In this way, the single actuating mechanism can be utilized to selectively apply either cervical or pelvic traction without modification.

In the preferred embodiment, the frame is an open rectangle which is articulated or hinged at its middle to allow folding for transportation. The actuating device is a hydraulic cylinder mounted along one side of the frame and actuated by a hand pump. A pressure relief valve is provided to assure that the patient cannot exceed a preselected traction force. A vertical post is mounted at one end of the frame for elevating the cervical harness during cervical traction. A counter-traction belt is attached to the same end of the frame for use during pelvic traction. An elevated leg rest is also provided at the other end of the frame so that the patient's legs may be raised during either cervical or pelvic traction.

DESCRIPTION OF THE PREFERRED EMBODIMENT

Figure 1:
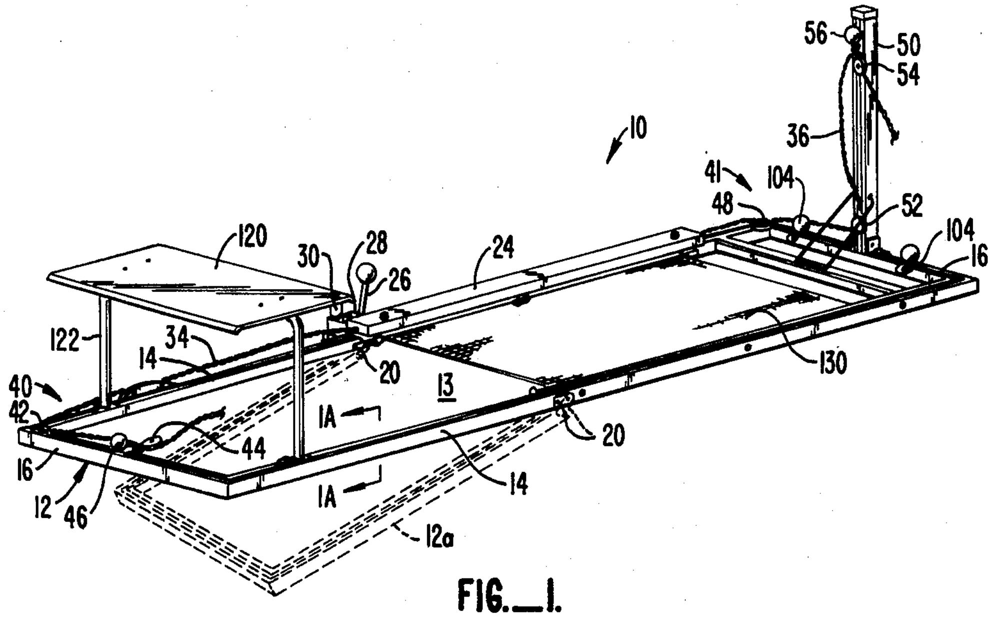
FIG. 1 is an isometric view of the traction system of the present invention with the partially folded configuration shown in broken line.
Figure 1A:
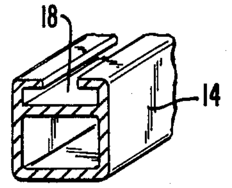
FIG. 1A is a sectional view taken along line 1A—1A in FIG. 1.

Referring to FIG. 1, a traction system 10 constructed in accordance with the principles of the present invention is illustrated. The system 10 includes an open frame 12 having a pair of side members 14 and end members 16 defining an open area 13. Both the side members 14 and end members 16 include a channel or track 18 formed on the upper surface thereof (FIG. 1A). All references to upward and downward directions made hereinafter in the specification and the claims will be in reference to the device in the orientation illustrated in FIG. 1. The channel 18 is provided to allow mounting of various components on the frame using carriage bolts (not illustrated), as will be described in more detail hereinafter.

The side members 14 are articulated about hinge members 20 so that the frame 12 may be folded in half for transportation. The partially folded forward section **12*a* of the frame 12 is illustrated in broken line in FIG. 1**.

A tension-applying mechanism 24 is mounted on one of the side members 14 on upper half (to the right in FIG. 1) of the frame 12. As will be described in more detail hereinafter, the tension-applying mechanism includes a handle 26, control box 28, and tension setting knob 30, which are utilized by the patient as the patient reclines in the open area 13 defined by the frame 12.

The traction system 10 further includes a pelvic traction cord 34 and cervical traction cord 36 which are each attached at one end to the tension-applying mechanism 24. The tension-applying mechanism 24 is able to retract each of the cords 34 and 36 to apply traction tension to the patient, as will be described in more detail hereinafter.

Figure 4:
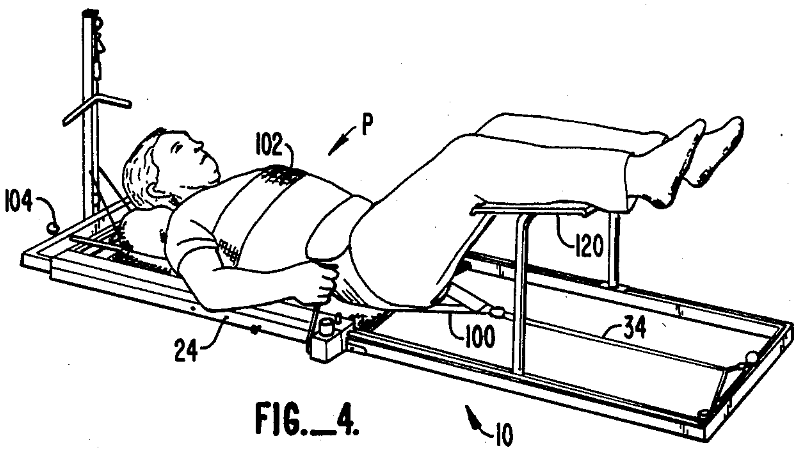
FIG. 4 is a perspective view illustrating a patient utilizing the traction system of the present invention for pelvic traction.

The pelvic traction cord 34 extends from the tension applying mechanism 24 toward the lower end 40 of the frame 12 (to the left in FIG. 1). The cord 34 extends around a pulley 42 at the junction of the side and end members 14 and 16. From there, the cord 34 extends to a movable pulley 44 which is attached to end member 16 by carriage bolt 46. The cord 34 is then attached to a pelvic traction belt (as illustrated in FIG. 4) for treatment of the patient. It will be appreciated that when the cord 34 is retracted by tension-applying mechanism 24, the remote end of the cord will be drawn toward the lower half of the frame 12. This is the desired direction for pelvic traction when the patient is lying with his or her head at the upper end 41 of the frame.

The cervical traction cord 36 extends from the tension-applying mechanism 24 toward the upper end 41 of the frame 12, where it extends around a fixed pulley 48. The cervical traction cord 36 is then directed upward on a vertical post 50 by passing around pulley 52 at the bottom end of said post and over pulley 54 at the top end of the post. The elevation of the upper pulley 54 may be adjusted by carriage bolt 56 which is mounted in a track on the post similar to track 18 on frame 12. In this way, the cervical traction harness (110 in FIG. 5) is elevated over the patient when the patient is lying in the frame 12.

Figure 2:
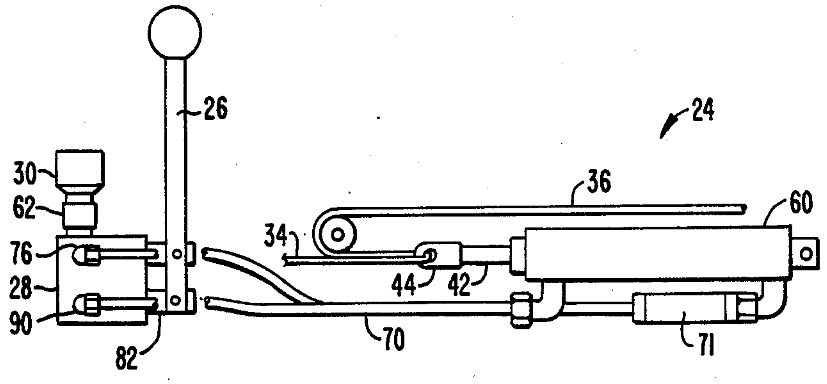
FIG. 2 is a schematic illustration of the hydraulic actuating system of the present invention.

The tension-applying mechanism 24 will now be described in greater detail with reference to FIGS. 2, 3A, and 3B. The tension-applying mechanism 24 comprises a hydraulic cylinder 60, the pump and control box 28, and a dump valve 62. The pump and control block 28 includes pump handle 26 and micrometer adjustment dial 30. Hydraulic line 70 connects the output of block 28 with the hydraulic cylinder 60 so that the piston therein realizes the full output pressure. Line 70 includes a surge bladder 71 which accomodates the excess oil which accumulates during operation of the pump 28. The normally-closed dump valve 62 allows the user to relieve pressure from the cylinder when it is desired to terminate treatment.

Figure 3A:
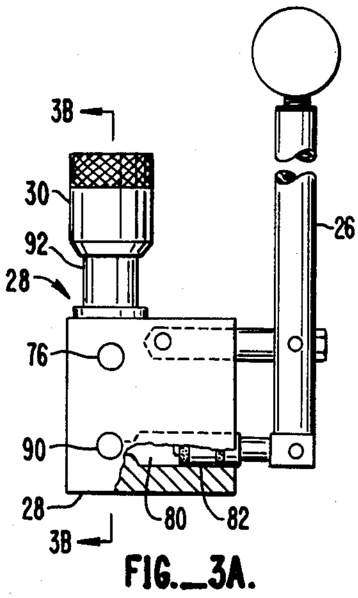
FIGS. 3A and 3B are illustrations of the control block of the hydraulic actuating system of the present invention.
Figure 3B:
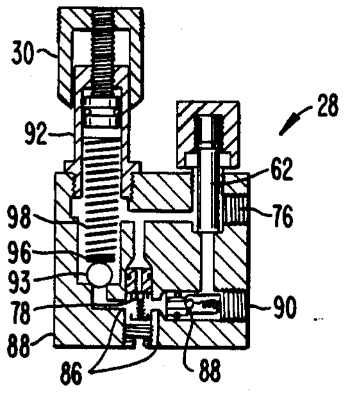

Referring now in particular to FIGS. 3A and 3B, the pump and control block 28 includes an inlet port 76 which is connected to one end of the cylinder 60. Oil is able to flow through port 76 and past an inlet check valve 78 into pump cylinder 80. A pump piston 82 is operatively connected to the pump handle 26 so that the user may reciprocate the piston to pressurize the oil in cylinder 80. The pressurized oil will pass outward through passage 86 where it may flow past an outlet check valve 88 through an outlet port 90 and to the other end of hydraulic cylinder 60 (see FIG. 2). Alternatively, the oil in passage 86 may flow past the adjustable relief valve 92, depending on its set-point and the pressure in the hydraulic line, as described hereinbelow. The relief valve 92 is a spring-loaded check valve (defined by seating ball 93 within the passage 86) where the compression on a spring 98 may be adjusted by the micrometer adjustment dial 30. Such adjustment results in variation on the pressure applied by ball pressure pad 96 by the spring 98. The ball 93 will remain seated over passage 86 until the pressure in the passage exceeds the force applied by spring 98 multiplied by the exposed area of the ball. When this occurs, the oil will flow past the ball 93 until the pressure is equalized. The adjustment dial 30 will typically be calibrated in pounds force applied by the cylinder 60 on the patient.

The pressure in the hydraulic cylinder 60 is a direct function of the tension on the associated cord 34 or 36. The tension on the cord is, of course, determined by the traction force being exerted on the patient. Thus, until both the patient 12 and the traction cable are under tension, the cylinder 60 will not be pressurized. As soon as either cord 34 or 36 begins to pull on the patient, however, the pressure in cylinder 60 immediately begins to rise. The tension, and the pressure in the cylinder 60, will continue to rise as the user reciprocates handle 26 until the pressure in cylinder 60 exceeds the set point of the adjustable relief valve 92.

The relief valve 92 will be calibrated in pounds tension applied by the cylinder to the patient, typically in the range from about 0 to 200 pounds. Such a range provides for both gentle cervical traction and for the necessary heavier pull for pelvic traction. Once reached, the desired traction force will be maintained by the hydraulic system. After a time, however, the patient may relax and by doing so relieve pressure from the system. Should this occur, the patient need merely work the pump a little bit more to restore the desired pressure to the system. The patient need not worry that excess traction will be applied since the relief valve prevents such overstressing.

Referring now to FIG. 4, the device 10 may be used by a patient P for pelvic traction utilizing a pelvic traction harness 110 at the end of pelvic traction cord 34. The pelvic traction belt 100 is placed around the patient's waist, and typically the patient will also wear a counter-traction belt 102 beneath his or her arms. The counter-traction belt 102 is secured to the head end member 16 on carriage bolts 104. The patient is able to apply tension to cord 34 using the tension-applying mechanism 24 as just described.

Figure 5:
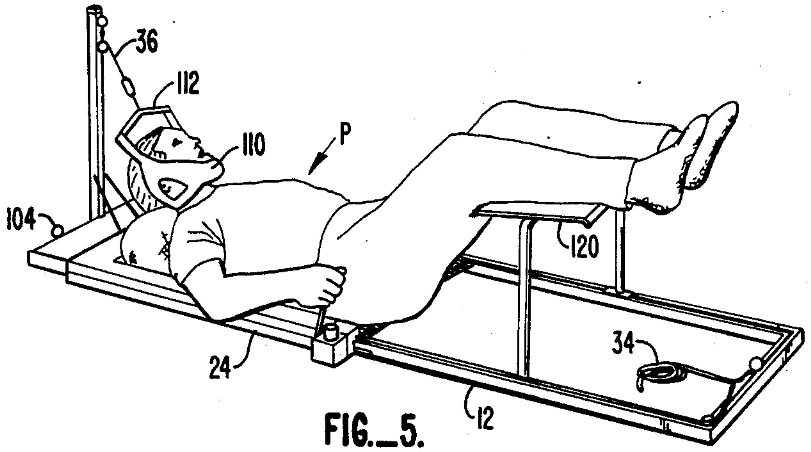
FIG. 5 is a perspective view illustrating a patient utilizing the traction system of the present invention for cervical traction.

Referring now to FIG. 5, the use of device 12 for applying cervical traction will be described. Patient P lies in substantially the same position as when utilizing the device for cervical traction, but wears only a single cervical harness 110 about the chin and head. The cervical harness 110 is attached to cervical traction cord 36 by a spreader bar 112, and the patient P can apply tension to the harness 110 using tension-applying mechanism 24, as just described. In both cases, the patient P will usually elevate his or her legs on a leg rest 120 supported on frame 12 by subframe 122. Subframe 122 is mounted in channel 18 of frame 12 so that its position may be changed as desired by the individual patient.

Traction device 10 may be disassembled and folded for transportation. The post 50 and leg rest 120 may be removed, and the frame 12 folded about hinges 20. A fabric sling 130 (FIG. 1) is detachably mounted in side frame and may be used for holding the loose components of the system 10 including the post 50, the leg rest 120, the cords 34 and 36, as well as the various braces. Also, when the patient P lies on the sling 130, the weight of the patient holds the device 10 in place on the mounting surface.

Although the foregoing invention has been described in some detail by way of illustration and example for purposes of clarity of understanding, it will be obvious that certain changes and modifications may be practiced within the scope of the appended claims.

What is claimed is:

1. A traction system comprising:

an elongate rigid frame having a pair of parallel, spaced-apart side members and first and second opposite ends and defining an open area of sufficient size to receive a reclining person;

a cervical harness attached to a tension cord;

a pelvic harness attached to a tension cord;

means mounted on one of the side members of the frame for applying tension to said tension cords;

means mounted on the frame about the periphery of the open area for threading the pelvic harness tension cord from the tension-applying means to the first end of the frame; and means mounted on the frame about the periphery of the open area for threading the cervical harness tension cord from the tension applying means to the second end of the frame.

2. A traction system as in claim 1, wherein the elongate frame is articulated to allow folding for transportation.

3. A traction system as in claim 1, wherein the tension applying means comprises a manually actuated hydraulic cylinder attached to both the cervical and pelvic tension cords.

4. A traction system as in claim 3, wherein the hydraulic cylinder is actuated by a manually operated pump.

5. A traction system as in claim 4, wherein the hydraulic cylinder and manual pump are attached to means for adjustably limiting the maximum force applied to the cylinder by the pump.

6. A traction system as in claim 3, wherein the tension-applying means further comprises means for bleeding the hydraulic cylinder to release the force.

7. A traction system as in claim 1, wherein the means for threading each comprises pulleys attached to the frame.

8. A traction system as in claim 7, wherein the means for threading the cervical tension cord further comprises a post for elevating the cervical harness relative to the frame.

9. A traction system as in claim 7, wherein the positions of at least some of the pulleys on the frame are adjustable.

10. A traction system comprising:

a flat rectangular frame having two side members and two end members; said frame being substantially open in the center;

a cervical harness attached to a tension cord;

a pelvic harness attached to a tension cord;

a hydraulic cylinder mounted on one side member of the frame and attached to both the cervical tension cord and the pelvic tension cord so that the cords are retracted when the cylinder is actuated;

a manually actuated pump mounted on the one side member and fluidly connected to actuate the hydraulic cylinder;

a plurality of pulleys mounted on the frame for threading the cervical harness cord to one end member of the frame and threading the pelvic harness cord to the other end member of the frame.

11. A traction system as in claim 10, further comprising a post detachably mounted on the one end member for elevating the cervical harness relative to the frame.

12. A traction system as in claim 10, further comprising a counter traction belt and means for securing the counter traction belt to the one end member.

13. A traction system as in claim 10, wherein the two side members are articulated to allow folding of the frame for transportation.

14. A traction system as in claim 10, further comprising a sling bag detachably mounted inside the frame.

15. A traction system as in claim 10, further comprising means for adjustably limiting the maximum force applied to the cylinder by the pump.

* * * * *